United States Patent [19]

Dermer

[11] 4,277,237
[45] Jul. 7, 1981

[54] JAW IMPLANT MEASURING INSTRUMENT

[76] Inventor: Saul R. Dermer, 3226 College Dr., Columbus, Ga. 31907

[21] Appl. No.: 141,765

[22] Filed: Apr. 21, 1980

[51] Int. Cl.³ ............................................. A61C 19/04
[52] U.S. Cl. .................................. 433/72; 33/174 D; 33/149 B
[58] Field of Search ................... 433/72, 173, 176, 72; 33/174 D, 149 B, 143 C

[56] References Cited

U.S. PATENT DOCUMENTS

| | | |
|---|---|---|
| 90,705 | 6/1869 | Bonhorst . |
| 1,006,660 | 10/1911 | Keppie . |
| 1,216,596 | 2/1917 | Nishi .................................. 33/147 D |
| 1,419,645 | 6/1922 | Santori . |
| 1,460,275 | 6/1923 | Belanger et al. . |
| 1,708,191 | 4/1929 | Riedel ............................... 33/149 B |
| 2,060,555 | 11/1936 | Coble .................................... 33/143 |
| 3,335,497 | 8/1967 | Stein et al. ......................... 33/149 B |
| 3,335,497 | 8/1967 | Stein et al. ................................ 33/27 |
| 3,879,849 | 4/1975 | Schwartz ....................... 33/143 C X |

Primary Examiner—Robert Peshock
Attorney, Agent, or Firm—Browdy & Neimark

[57] ABSTRACT

A dental instrument for facilitating the selection and implantation of a generally U-shaped denture-supporting implant frame with bendable side arms. The instrument is generally similar to bow dividers, but is provided with an extensible calibrated distance bar which is supported for longitudinal adjustment in a median plane perpendicular to the plane of the main divider legs for movement parallel thereto, the distance bar having a pointed depending arm to locate a front center point on a patient's mandible adapted to receive an implantable front lug on the implant frame. This enables necessary data to be obtained for selecting the proper size of implant frame and for shaping the side arms of the implant frame so that they correspond with the shape of the patient's mandible.

10 Claims, 9 Drawing Figures

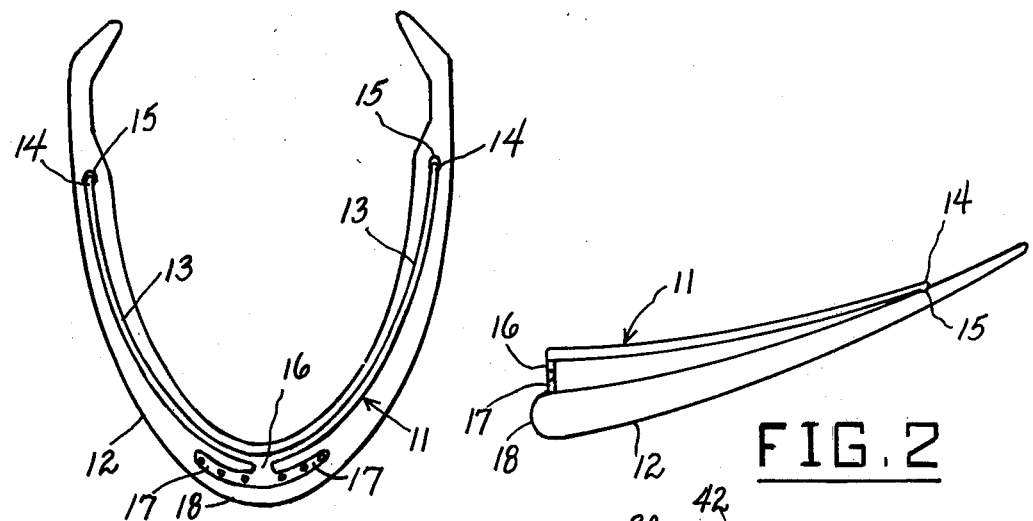
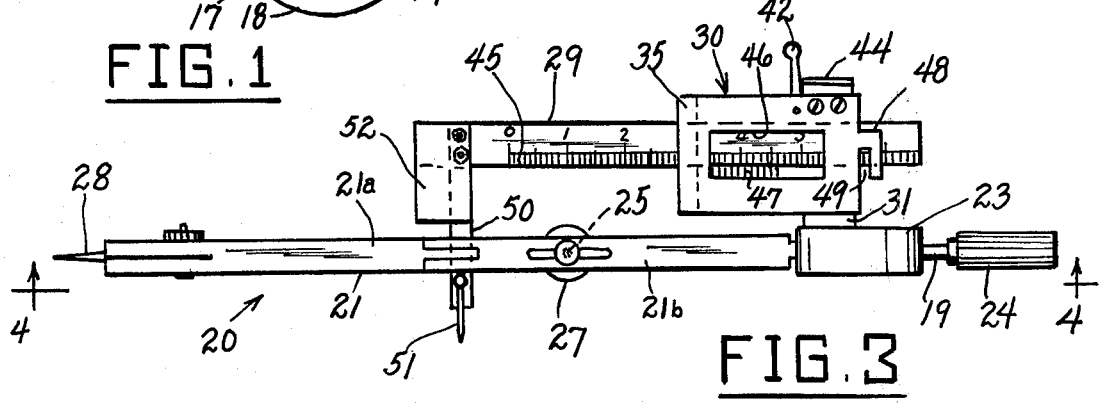
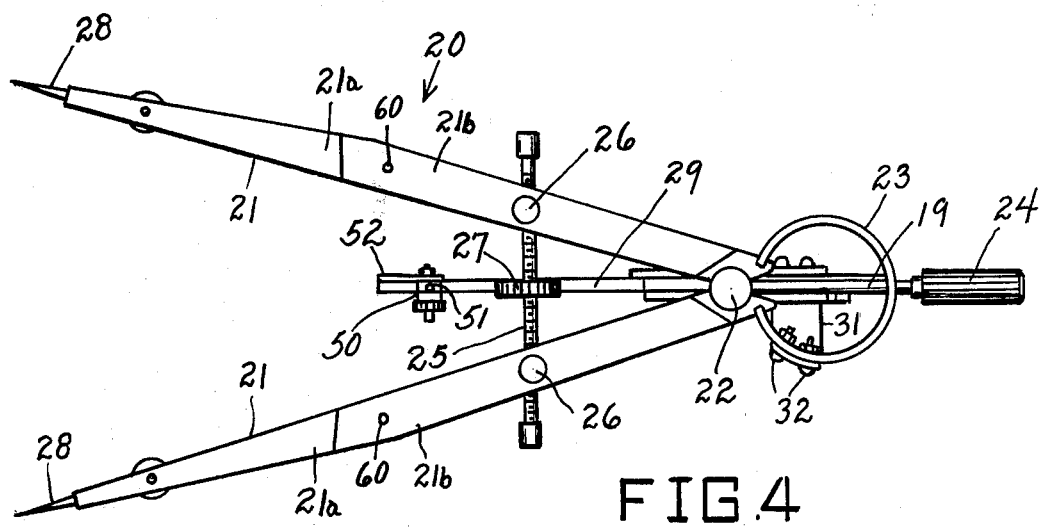

JAW IMPLANT MEASURING INSTRUMENT

FIELD OF THE INVENTION

This invention relates to dental instruments, and more particularly to a measuring device to enable the proper selection and fitting of a jaw implant intended as a denture support.

BACKGROUND OF THE INVENTION

At the present time there are available commercially manufactured jaw implant frame devices intended to be implanted in a patient's mouth and to serve subsequently as supports for artificial teeth or dentures. As an example, "Ramus Frames" are available, made by United Implant Ltd., Vancouver, B.C., Canada. These frame devices are generally U-shaped and are made with adjustably bendable implantable side arms and with implantable front lugs adapted to respectively supportingly engage with the rear side and front portions of a patient's mandible. The devices are made in different sizes and heretofore have been selected and adjusted in shape mainly by trial and error, consuming a great deal of time in selecting the proper size and shaping the device in order to properly fit a patient, accompanying this with considerable discomfort on the part of the patient. Thus, it has been necessary to ascertain (a) what size implant to use, (b) at what angles to bend the frame side arms so that their ends properly engage with the rear end portions of the patient's jaw, and (c) where to locate the front tissue channel so that the front of the frame is substantially perpendicularly positioned relative to the jaw. To date, proper placement of the Ramus Frame implant has been a highly demanding task for the dental surgeon and has required a large measure of skill and precision on the part of the surgeon. Thus, even practitioners with a maximum amount of experience in this operation have expressed the need for a device to aid in the fitting of the Ramus Frame. Heretofore there has been no adequate instrument to fill this need.

As a result of a preliminary search of the prior art, the following prior U.S. patents of interest were located, which appear to show the current state of the art:

Bonhorst, U.S. Pat. No. 90,705
Keppie, U.S. Pat. No. 1,006,660
Santori, U.S. Pat. No. 1,419,645
Belanger et al, U.S. Pat. No. 1,460,275
Riedel, U.S. Pat. No. 1,708,191
Coble, U.S. Pat. No. 2,060,555
Stein et al, U.S. Pat. No. 3,335,497
Schwartz et al, U.S. Pat. No. 3,879,849

SUMMARY OF THE INVENTION

Accordingly, a main object of the invention is to provide a novel and improved jaw implant measuring instrument which overcomes the disadvantages and deficiencies of previously employed measuring devices used for the jaw implant operation.

A further object of the invention is to provide an improved instrument for measuring a patient's mouth to determine the required size and configuration of a Ramus Frame implant to be used for forming a support for an artificial denture.

A still further object of the invention is to provide an improved oral measuring instrument for determining what size implant frame is to be used, to what angles to bend the size arms of the implant frame so that their ends can be properly implanted against the patient's jaw, and where to prepare the front implant channel so that the front element of the implanted frame rises substantially perpendicularly from the front of the patient's jaw.

A still further object of the invention is to provide an improved dental instrument for selecting the size of and for facilitating the proper shaping of an implantable denture-supporting frame of the Ramus Frame type, the instrument being relatively easy to use, providing accurate and reproducible frame positioning data, greatly facilitating the placement of such an implant in a patient's mouth, and minimizing the discomfort of the patient during the frame-selecting procedure.

A still further object of the invention is to provide an improved dental instrument generally similar to bow dividers, but provided with an extensible calibrated distance bar adjustable in a perpendicular median plane between the main arms of the instrument, the calibrated distance bar having a pointed depending arm to locate a front center point on a patient's mandible adapted to receive an implantable front frame lug, thereby enabling the necessary data to be obtained for selecting the proper size of implant frame and for shaping the side arms of the implant frame so that they correspond with the shape of the patient's mandible.

A still further object of the invention is to provide an improved measuring instrument for facilitating the proper selection and shaping of a denture-supporting implant of the Ramus Frame type and for determining the insertion angles for installing the implant.

BRIEF DESCRIPTION OF THE DRAWINGS

Further objects and advantages of the invention will become apparent from the following description and claims, and from the accompanying drawings, wherein:

FIG. 1 is a top perspective view of a model of a typical mandible showing an implantable Ramus Frame disposed thereon, and illustrating the relative positions thereof when the frame is substantially in implant position.

FIG. 2 is a side elevational view of the mandible model and Ramus Frame shown in FIG. 1.

FIG. 3 is a side elevational view of a typical dental measuring instrument according to the present invention, for measuring a mandible and obtaining the data required for fitting an implant frame thereto.

FIG. 4 is a bottom view of the instrument, taken substantially on the line 4—4 of FIG. 3.

DESCRIPTION OF A PREFERRED EMBODIMENT

Figure 5:
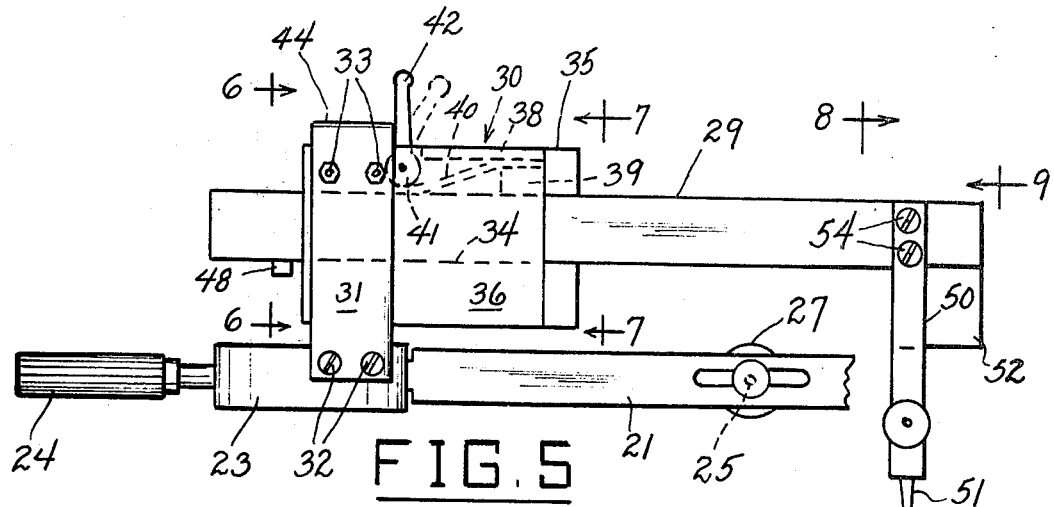
FIG. 5 is an enlarged fragmentary side elevational view of the instrument taken from the side opposite to that of FIG. 3.

Referring to the drawings, FIGS. 1 and 2 show a typical Ramus Frame 11 in relation to a model mandible 12, representing the general manner in which the Ramus Frame must be implanted in the patient's mouth in order to be properly supported on a mandible. It will be seen that the Ramus Frame 11 is generally U-shaped and that its side arms 13, 13 should be shaped so as to generally conform with the side portions of the mandible, with the tips 14, 14 engaged on the rear portions of the mandible side arms, for example, in relatively shallow sockets 15, 15 formed in said mandible side arm rear portions. The typical Ramus Frame 11 has a depending front center lug 16 with apertured laterally extending wings 17, 17 adapted to be embedded in a channel formed in the tissue directly above the front portion 18 of the mandible. As shown in FIG. 2, the implanted depending front lug 16 should extend substantially perpendicularly to the front mandible portion 18 on which it rests, with the tips 14, 14 embedded in the tissue so as to engage in the sockets 15, 15, for optimum positioning of the implanted frame 11.

Ramus Frames are commercially manufactured in various sizes, to cover the range of mandible sizes of different individuals, and are suitably numbered as to size. In order to select the proper implant size it is necessary to measure the patient's mouth to determine the relative locations of the implant areas, corresponding to the final optimum positions of tips 14, 14 and lug 16. This data enables the selection of the frame size required for a proper fit, as well as providing the information for the required bending of the frame side arms 13, 13 to shape the frame so as to generally conform to the shape of the patient's mandible and to provide the correct insertion angles for installing the implant.

An instrument for performing the required measurement is designated generally at 20. The instrument 20 comprises a main portion resembling conventional bow dividers, such main portion having a pair of opposite divider legs 21, 21 suitably shaped to interengage at their right ends, as viewed in FIG. 4, with a fulcrum pin 22 and being clamped thereto by a strong C-shaped generally circular spring 23. The legs 21 are each formed of two sections 21a and 21b joined by a pivot pin 60 to permit angular adjustment. An axial rod 19 is rigidly connected to the fulcrum pin 22 and extends diametrically through the spring 23, and is provided with a gripping handle 24, as in conventional bow dividers. A transverse turnbuckle shaft 25 is threadedly engaged with respective pivoted bearing pins 26, 26 provided in the opposite legs 21, 21, and has an integral central adjusting disc 27 with a serrated periphery, the turnbuckle shaft 25 being oppositely threaded on the opposite sides of disc 27 in the same manner as in conventional bow dividers, for adjusting the angle between the legs 21, 21, thereby adjusting the spacing between respective sharp points 28, 28 adjustably clamped on the free ends of said legs. The structure thus far described is substantially the same as in conventional bow dividers.

Designated at 29 is a longitudinal scale bar which is adjustably supported for longitudinal adjustment in a median plane perpendicular to the plane defined by the divider legs 21, 21 and which is constrained for movement parallel to said plane. Thus, the scale bar 29 is slidably mounted in a relatively flat rectangular guide sleeve assembly, designated generally at 30, which is rigidly secured to the generally circular spring 23 by an upstanding rigid bracket bar 31, as shown in FIG. 5. The lower end of bracket bar 31 is rigidly fastened to ring 23 by a pair of bolts 32, 32. The bracket bar 31 is shaped so that its top portion is adjacent to and parallel with said median plane perpendicular to the plane of legs 21, 21, and is rigidly secured by bolts 33, 33 to the left end portion of the generally rectangular guide sleeve assembly 30, as viewed in FIG. 5. Guide sleeve assembly 30 has a rectangular guide channel 34 slidably receiving bar 29 and formed to support it for movement parallel to the plane of the divider legs in said median plane.

Figure 7:
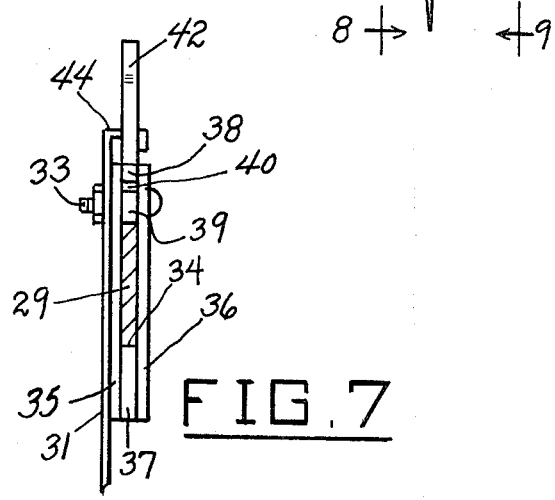
FIG. 7 is an enlarged transverse vertical cross-sectional view taken substantially on line 7—7 of FIG. 5.
Figure 8:
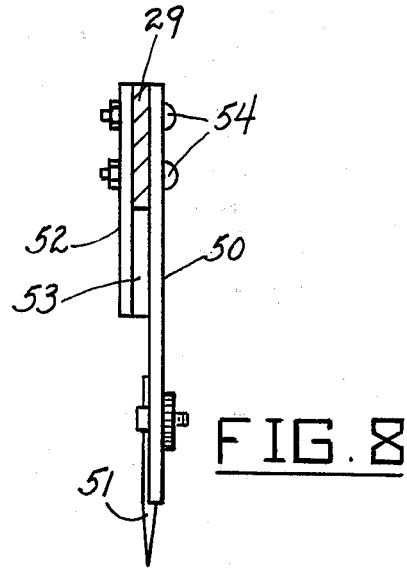
FIG. 8 is an enlarged transverse vertical cross-sectional view taken substantially on line 8—8 of FIG. 5.

In the typical embodiment illustrated in the drawings, the guide sleeve assembly 30 comprises a substantially rectangular first side plate 35, a substantially rectangular second side plate 36, and a bottom spacer plate 37 welded between the lower margins of the side plates 35, 36, as shown in FIG. 7. Rigidly secured between the upper marginal portions of plates 35, 36 are a top longitudinal spacer strip 38 and an end spacer block 39. The end portion of a friction spring 40 is rigidly secured between strip 38 and block 39 and extends into frictional contact with the top edge of scale bar 29, as shown in FIG. 5. A locking cam 41 is pivoted in the recess defined between top strip 38 and scale bar 29, said cam having an operating handle 42. When handle 42 is rotated to its dotted view position in FIG. 5, the scale bar 29 is clamped in fixed position by cam 41 because of the clamping pressure on spring 40 exerted by said cam.

Figure 6:
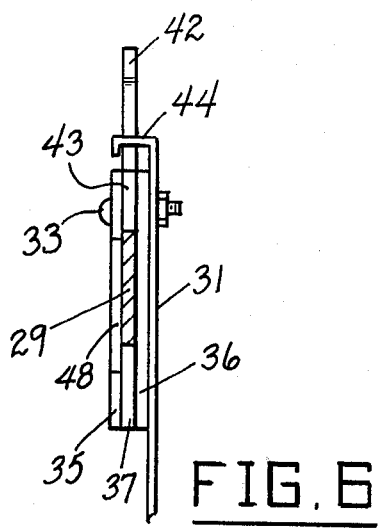
FIG. 6 is an enlarged transverse vertical cross-sectional view taken substantially on line 6—6 of FIG. 5.

Another spacer block 43 is secured between the upper left end marginal portions of plates 35, 36, as viewed in FIG. 5 (see FIG. 6).

Bracket bar 31 is formed with a channel-shaped top flange 44 which is located to act as a rear stop abutment for handle 42 and which limits the rotation of the handle rearwardly to the full-line position of FIG. 5, wherein scale bar 29 is free to slide in channel 34, except for the normal frictional retarding action of spring 40.

Scale bar 29 is provided with a distance scale 45 calibrated in suitable length units, such as centimeters, and plate 35 is formed with a corresponding longitudinal scale-viewing window 46 having a vernier scale 47 at its lower edge, as shown in FIG. 3. Plate 35 is provided with a rear lug 48 overlying scale 45 and having a vertical marking notch 49 for marking the scale with a pencil, crayon, or the like, to indicate a particular setting of scale bar 29 for future reference, if so desired.

Figure 9:
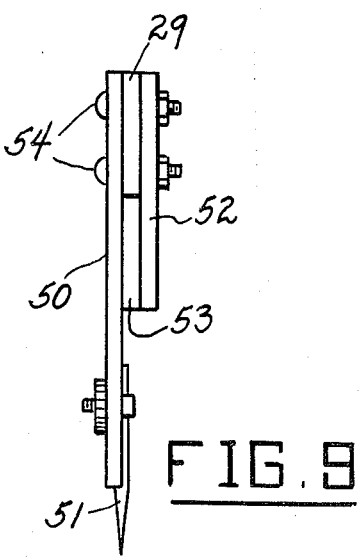
FIG. 9 is an enlarged end elevational view taken substantially on line 9—9 of FIG. 5.

Rigidly secured perpendicularly to the forward end of scale bar 29 (its rightward end, as viewed in FIG. 5) is a depending arm 50 having a sharp-pointed pin 51 adjustably clamped thereto. A rectangular backing plate 52 may be employed opposite arm 50, provided with a space block 53 underlying scale bar 29 and filling the space between plate 52 and arm 50, as shown in FIG. 9. The top portion of arm 50, scale bar 29 and backing plate 52 may be rigidly secured together by a pair of vertically spaced bolts 54, 54, as shown in FIGS. 5 and 9.

In using the instrument 20 to aid in the fitting of a Ramus Frame implant, the following procedure may be employed:

1. The three metal pointed tips 28, 28 and 51 are clamped in operative projecting positions and the instrument is adjusted in such a manner that the tips can be engaged on the specific jaw sites intended to receive the tissue implant portions of the intended frame. This involves longitudinal adjustment of the scale bar 29, vertical adjustment of the pointed tip 51, angular adjustment of the legs 21, 21, and axial adjustment of the pointed tips 28, 28.

2. From the above measurement, it is possible to determine which size (for example, No. 4, No. 5, No. 6 or No. 7) Ramus Frame would be best suited for final fit. In many cases, more than one size frame could be fitted to a patient's jaw. The device 20 aids in achieving the correct adaptation.

3. With the patient under anesthesia and with the pointed tips located in their adjusted positions, the device 20 is inserted in the patient's mouth in a position with the points at the abovementioned jaw sites, and then the device is manipulated so that the points penetrate through the tissue onto the bone. The device is then removed. The spots of tissue penetration will show up very clearly when the device is removed. Then a burr in a dental handpiece can be employed to follow the angular orientation of the spots and to suitably perforate the tissue and mark the bone (for example, to form shallow sockets 15, 15, as shown in FIG. 1, for subsequent engagement by the frame tips 14, 14.

4. With the corrected adjustment of the device 20, as above described, the bends of the rear portions of the Ramus Frame can be made quite accurately, for example, by making a pattern on graph paper and bending the side arms 13, 13 of the frame to conform with said pattern.

5. Once the tissue has been opened to expose the bone in each back area of the patient's jaw, the tissue mark made by the center pointed tip 51 locates the position of the required tissue channel which must be prepared to receive the front lug 16 of the frame. Thus, the frame may be inserted, with the tips 14, 14 and the lug 16 respectively properly oriented to be received in the respective rear tissue perforations and the front tissue channel.

The employment of the device 20 greatly aids in the determination of the location and required direction of the tissue channel which must be prepared to receive the front lug 16 of the Ramus Frame. If the channels made in the back of a patient's jaw and the bends of the Ramus Frame implant in these areas are not accurate, there would be enormous difficulty in preparing the tissue for receiving the front support lug of the implant and for insuring its proper seating. Heretofore, most of the time and effort involved in the placement of the Ramus Frame has been concerned with the above problem. The use of the device 20, as above described, substantially solves said problem, thus saving a considerable amount of time and avoiding much frustration.

While a specific embodiment of an improved jaw implant measuring instrument has been disclosed in the foregoing description, it will be understood that various modifications within the scope of the invention may occur to those skilled in the art. Therefore it is intended that adaptations and modifications should and are intended to be comprehended within the meaning and range of equivlents of the disclosed embodiment.

What is claimed is:

1. A dental instrument for measuring a patient's jaw to determine the size, configuration and implantation locations of an implantable denture-supporting frame of the type comprising a generally U-shaped body with a pair of rear end tips and a depending front support lug, said instrument comprising a pair of main legs, pivot joint-defining means pivotally connecting the front ends of the main legs, means for adjusting the angle between said main legs, said main legs having pointed marking elements on their free ends, guide sleeve means having an elongated guide channel, means rigidly supportingly connecting said guide sleeve means to said joint-defining means with said guide channel extending substantially in the median plane perpendicular to the plane of the main legs and extending in an axial direction parallel to the plane of the main legs, a longitudinally adjustable slide bar mounted in said guide channel, a depending arm secured to said slide bar and extending between said main legs substantially in said median plane, and marking point means on the bottom end of said depending arm.

2. The dental instrument of claim 1, and wherein said marking point means comprises a pointed pin element adjustably clamped to the bottom end of said depending arm.

3. The dental instrument of claim 1, and wherein said guide sleeve means comprises a relatively flat sleeve located substantially in said median plane.

4. The dental instrument of claim 3, and means on said flat sleeve clampingly engageable with said slide bar at times to lock the slide bar in adjusted position.

5. The dental instrument of claim 3, and wherein said slide bar is provided with a length scale, and index means on the flat sleeve located to cooperate with said length scale.

6. The dental instrument of claim 5, and wherein said index means comprises a longitudinal viewing window formed in one side of said flat sleeve, and a vernier scale on one longitudinal edge of said window.

7. The dental instrument of claim 1, and wherein said depending arm is perpendicularly rigidly secured to an end of the slide bar.

8. The dental instrument of claim 1, and locking means on said guide sleeve means to exert locking force on said slide bar to lock the slide bar in longitudinally adjusted position.

9. The dental instrument of claim 8, and retarding spring means in the guide sleeve means frictionally engaging said slide bar.

10. The dental instrument of claim 9, and wherein said spring means is located between a longitudinal edge of said slide bar and said locking means.

* * * * *